(12) United States Patent
Kitano et al.

(10) Patent No.: US 8,911,352 B2
(45) Date of Patent: Dec. 16, 2014

(54) ENDOSCOPE-HOLDING DEVICE AND ENDOSCOPIC SYSTEM

(75) Inventors: Seigo Kitano, Beppu (JP); Kazuhiro Yasuda, Oita (JP); Takahiro Kogasaka, Tokyo (JP); Kunihide Kaji, Tokyo (JP); Ken Yamatani, Tokyo (JP); Nobuko Matsuo, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 65 days.

(21) Appl. No.: 13/352,394

(22) Filed: Jan. 18, 2012

(65) Prior Publication Data

US 2012/0232336 A1    Sep. 13, 2012

Related U.S. Application Data

(63) Continuation of application No. PCT/JP2011/065562, filed on Jul. 7, 2011.

(60) Provisional application No. 61/362,900, filed on Jul. 9, 2010.

(51) Int. Cl.
| | | |
|---|---|---|
| A61B 1/00 | (2006.01) | |
| A61B 1/313 | (2006.01) | |
| A61B 1/32 | (2006.01) | |
| A61B 17/02 | (2006.01) | |
| A61B 1/04 | (2006.01) | |
| A61B 17/00 | (2006.01) | |
| A61B 1/005 | (2006.01) | |

(52) U.S. Cl.
CPC ... *A61B 1/00098* (2013.01); *A61B 2017/00902* (2013.01); *A61B 1/00154* (2013.01); *A61B 1/00087* (2013.01); *A61B 17/00234* (2013.01); *A61B 2017/00296* (2013.01); *A61B 1/3132* (2013.01); *A61B 1/0055* (2013.01); *A61B 1/00089* (2013.01); *A61B 2017/00323* (2013.01); *A61B 1/32* (2013.01); *A61B 17/0218* (2013.01); *A61B 1/0057* (2013.01)
USPC ............ 600/102; 600/114; 600/127; 600/129

(58) Field of Classification Search
USPC ......... 600/104, 105, 107, 114–116, 120, 135, 600/153, 185–199
See application file for complete search history.

(56) References Cited

U.S. PATENT DOCUMENTS 5,716,321 A    2/1998 Kerin et al.
6,293,908 B1 *  9/2001 Fujikura et al. ............... 600/114
(Continued)

FOREIGN PATENT DOCUMENTS

EP    0 980 673 A2    2/2000
JP    62-22623 A      1/1987
(Continued)

OTHER PUBLICATIONS

European Search Report dated Jan. 28, 2013 from corresponding European Patent Application No. 11 80 3656.5.

(Continued)

*Primary Examiner* — Alireza Nia
(74) *Attorney, Agent, or Firm* — Scully, Scott, Murphy & Presser, P.C.

(57) ABSTRACT

An endoscope holding device includes an insertion part that is long and holds the distal end part of an endoscope so as to freely protrude and retract; a distal end face that specifies a protruding direction of the endoscope, and is formed at the distal end of the insertion part, a displacement part which has a displacement face that is curved from the distal end toward a proximal end and provided at a position apart from the distal end face in order to displace living body tissue in front of the insertion part to secure a space for operating the distal end part of the endoscope protruded from the distal end face to curve; and a fixing portion that fixes the displacement part and the insertion part such that the distal end side of the displacement face intersects a direction orthogonal to the distal end face.

16 Claims, 10 Drawing Sheets

(56) References Cited

U.S. PATENT DOCUMENTS

| | | | |
|---|---|---|---|
| 6,520,939 B2* | 2/2003 | Lafontaine | 604/167.03 |
| 7,261,728 B2* | 8/2007 | Long et al. | 606/207 |
| 2004/0019252 A1* | 1/2004 | Hirata | 600/114 |
| 2006/0268570 A1 | 11/2006 | Vayser et al. | |
| 2007/0135803 A1 | 6/2007 | Belson | |

FOREIGN PATENT DOCUMENTS

| | | |
|---|---|---|
| JP | S62-292135 A | 12/1987 |
| JP | 3-36602 U | 4/1991 |
| JP | 5-501660 A | 4/1993 |
| JP | 8-547 A | 1/1996 |
| JP | 10-511589 A | 11/1998 |
| JP | 11-56765 A | 3/1999 |
| JP | 2000-37347 A | 2/2000 |
| JP | 2000-507119 A | 6/2000 |
| JP | 2001-517962 A | 10/2001 |
| JP | 2002-501784 A | 1/2002 |
| JP | 2002-272677 A | 9/2002 |
| JP | 2005-185309 A | 7/2005 |
| JP | 2009-507617 A | 2/2009 |
| WO | WO 91/07201 A1 | 5/1991 |

OTHER PUBLICATIONS

English language abstract only of WO 96/20749 A1.
English language abstract only of WO 99/38463 A2.
English language abstract only of WO 97/29680 A1.
International Search Report PCT/JP2011/065562 dated Oct. 11, 2011.
Japanese Office Action dated Feb. 21, 2012 from corresponding Japanese Patent Application No. 2012-502365.
Notice of Allowance dated May 29, 2012 received from the Japanese Patent Office from related Japanese Patent Application No. 2012-502365, together with an English translation.

* cited by examiner

ENDOSCOPE-HOLDING DEVICE AND ENDOSCOPIC SYSTEM

This application is a Continuation application based on a PCT Patent Application No. PCT/JP2011/065562, filed on Jul. 7, 2011, claiming priority based on Provisional Application No. 61-362,900, filed in US on Jul. 9, 2010, the contents of both the PCT Application and the Provisional Application are incorporated herein by reference.

BACKGROUND OF THE INVENTION

1. Field of the Invention

The present invention relates to an endoscope holding device that is used by an endoscope insertion part being inserted into, and an endoscope system including the endoscope holding device and an endoscope.

2. Background Art

In the related art, various kinds of low-invasive medical treatment are being considered in order to reduce the burden given to a patient in the case of a procedure. There is a procedure referred to as a "Natural Orifice Translumenal procedure" as an example of the low-invasive medical treatment, and recently, a surgical case of the Natural Orifice Translumenal procedure is increasing. In this procedure, an endoscope is inserted into a patient's body through a natural opening, such as the mouth or anus or the like of a patient. A through hole for inserting this endoscope into a body cavity is formed, for example, in the alimentary canal wall. The endoscope and a treatment tool are introduced into the body cavity through this through hole to treat living body tissue.

In the Natural Orifice Translumenal procedure, postoperative recovery of a patient is fast since a surgical tool is inserted into the body cavity from the natural opening. On the other hand, in the Natural Orifice Translumenal procedure, a treatment is performed within the body cavity by the surgical tool inserted from the natural opening. Therefore, the surgical tool is limited and it is difficult to perform tasks. Particularly when a surrounding internal organ that becomes a hindrance to a procedure needs to be moved significantly, it is difficult to secure the operative field.

In order to improve this situation, for example, a multifunctional instrument (overtube) is disclosed in FIG. 10 of Japanese Translation of PCT International Application Publication No. H10-511589. This overtube includes an elongated tubular inside member (inside tubular member), a tubular outside member (outside tubular member) that is coaxially arranged around this inside member, and an expansion member (expandable member) having two finger portions. The expansion member is a member provided so as to be expandable. The two finger portions of the expansion member are tilted outward such that the distal ends thereof are separated from each other.

An opening is formed between the two finger portions. The far end of a control tube arranged inside the inside member is connected to the opening, and both communicate with each other. The inner cavity of the control tube configured in this way becomes a work channel, so that an imaging instrument such as an endoscope can be introduced into the control tube.

A fluid flows between the inside member and the control tube. As this fluid flows into the expansion member, the expansion member expands in a two-finger type. The expansion member contracts as the fluid flows out of the expansion member.

The expansion member is stored in advance inside the outside member. When a treatment is performed within a body cavity, the outside member is moved in an axial direction with respect to the expansion member. This allows the expansion member to be taken out from the inside of the outside member. In this state, the finger portions receive a tissue or an organic structure within the body cavity by expanding the expansion member. Thereby, a working space can be secured and various kinds of treatment can be performed.

SUMMARY OF THE INVENTION

According to a first aspect of the invention, an endoscope holding device includes an insertion part that is long and holds the distal end part of an endoscope so as to freely protrude and retract; a distal end face that specifies a protruding direction of the endoscope, and is formed at the distal end of the insertion part; a displacement part which has a displacement face that is curved from the distal end toward the proximal end and provided at a position apart from the distal end face in order to displace living body tissue in front of the insertion part in order to secure a space for operating the distal end part of the endoscope protruded from the distal end face to curve; and a fixing portion that fixes the displacement part and the insertion part such that the distal end side of the displacement face intersects a direction orthogonal to the distal end face.

According to a second aspect of the invention, in the endoscope holding device, the displacement face is provided at a plate-like body.

According to a third aspect of the invention, in the endoscope holding device, the plate-like body is formed so as to be larger than the external diameter of the insertion part in a width direction of the plate-like body specified in a direction parallel to the distal end face.

According to a fourth aspect of the invention, the endoscope holding device further includes a locking portion that is provided at the distal end side of the displacement part and regulates operation in a direction different from the advance and retreat directions of the endoscope.

According to a fifth aspect of the invention, an airtight valve is provided within the insertion passage.

According to a sixth aspect of the invention, the locking portion is a through hole formed at the distal end of the displacement part.

According to a seventh aspect of the invention, the through hole is formed with a size such that the endoscope insertion part is able to be inserted thereinto.

According to an eighth aspect of the invention, the through hole is provided on the center axis of the insertion passage at the distal end of the insertion passage.

According to a ninth aspect of the invention, the through hole is formed at a position and with a size such that the endoscope insertion part is able to be inserted thereinto while being made to slide in a plurality of ranges around its own outer peripheral surface.

According to a tenth aspect of the invention, an edge of the through hole in the displacement part is formed in a shape that has a curved surface that is convex in a thickness direction of the edge.

According to an eleventh aspect of the invention, the insertion part is formed from a hard material as a whole.

According to a twelfth aspect of the invention, the insertion part is straight.

According to a thirteenth aspect of the invention, the insertion part has a curving portion capable of being curved in a longitudinal direction of the insertion part, and a manipulating part which is configured to fix the curving portion in a predetermined curving state is provided.

According to a fourteenth aspect of the invention, the displacement part has a frame body formed from a hard material.

According to a fifteenth aspect of the invention, the displacement part has a plate-like body that occludes at least a parts of a space formed at the center of the frame body.

According to a sixteenth aspect of the invention, in the endoscope holding device described in the fifteenth aspect, the plate-like body is formed from a material having light permeability.

According to a seventeenth aspect of the invention the plate-like body is formed such that a range occupied by the plate-like body includes a range occupied by an inner cavity of the insertion part, in the width direction of the plate-like body, as seen from a direction parallel to the center axis of the insertion part.

According to an eighteenth aspect of the invention, the length of the outer periphery in a cross-section orthogonal to the longitudinal direction of the insertion part of the displacement part is set to be equal to or less than the length of the outer periphery of the insertion part.

According to a nineteenth aspect of the invention, the displacement part has a proximal end portion connected to the insertion part, a distal end portion which has the locking portion, and an intermediate portion that connects the proximal end portion and the distal end portion, and the distal end portion of the displacement part extends to the side closer to the center axis of the insertion passage than the intermediate portion of the displacement part or to the side exceeding the center axis.

According to a twentieth aspect of the invention, the intermediate portion of the displacement part is arranged at a position farther from the center axis of the insertion passage than the proximal end portion of the displacement part in the longitudinal direction of the insertion part.

According to a twenty-first aspect of the invention, the outer periphery of the displacement part is formed to have a predetermined curvature radius or more, and the outer periphery of a cross-section of the displacement part orthogonal to the longitudinal direction of the insertion part is formed to be equal to or more than the predetermined curvature radius, as seen from a direction orthogonal to the center axis of the insertion part.

According to a twenty-second aspect of the invention, the displacement part is configured so as to be rotatable around an axis that intersects the center axis of the insertion part.

According to a twenty-third aspect of the invention, the locking portion is formed at a position apart by a predetermined distance forward from the opening portion.

According to a twenty-fourth aspect of the invention, an endoscope system includes the endoscope holding device of the fifth aspect, and an endoscope which has an endoscope insertion part capable of being inserted into the insertion passage of the endoscope holding device.

According to a twenty-fifth aspect of the invention, the endoscope insertion part has an endoscope curving portion capable of being curved at the distal end thereof, and the length of the insertion part of the displacement part in the longitudinal direction is made equal to or more than the curving length of the endoscope curving portion.

According to a twenty-sixth aspect of the invention, indexes are provided in the longitudinal direction of the endoscope insertion part in the endoscope insertion part.

PREFERRED EMBODIMENTS

A first embodiment of an endoscope system related to the invention will be described below with reference to FIGS. 1 to 13. This endoscope system is used for a Natural Orifice Translumenal procedure. That is, this endoscope system is used to observe the inside of a body cavity with an endoscope and to perform an endoscopic treatment while securing an operative field by an endoscope holding device. The explanation of the embodiment of the invention will be described using an overtube as an example of an endoscope holding device.

Figure 1:
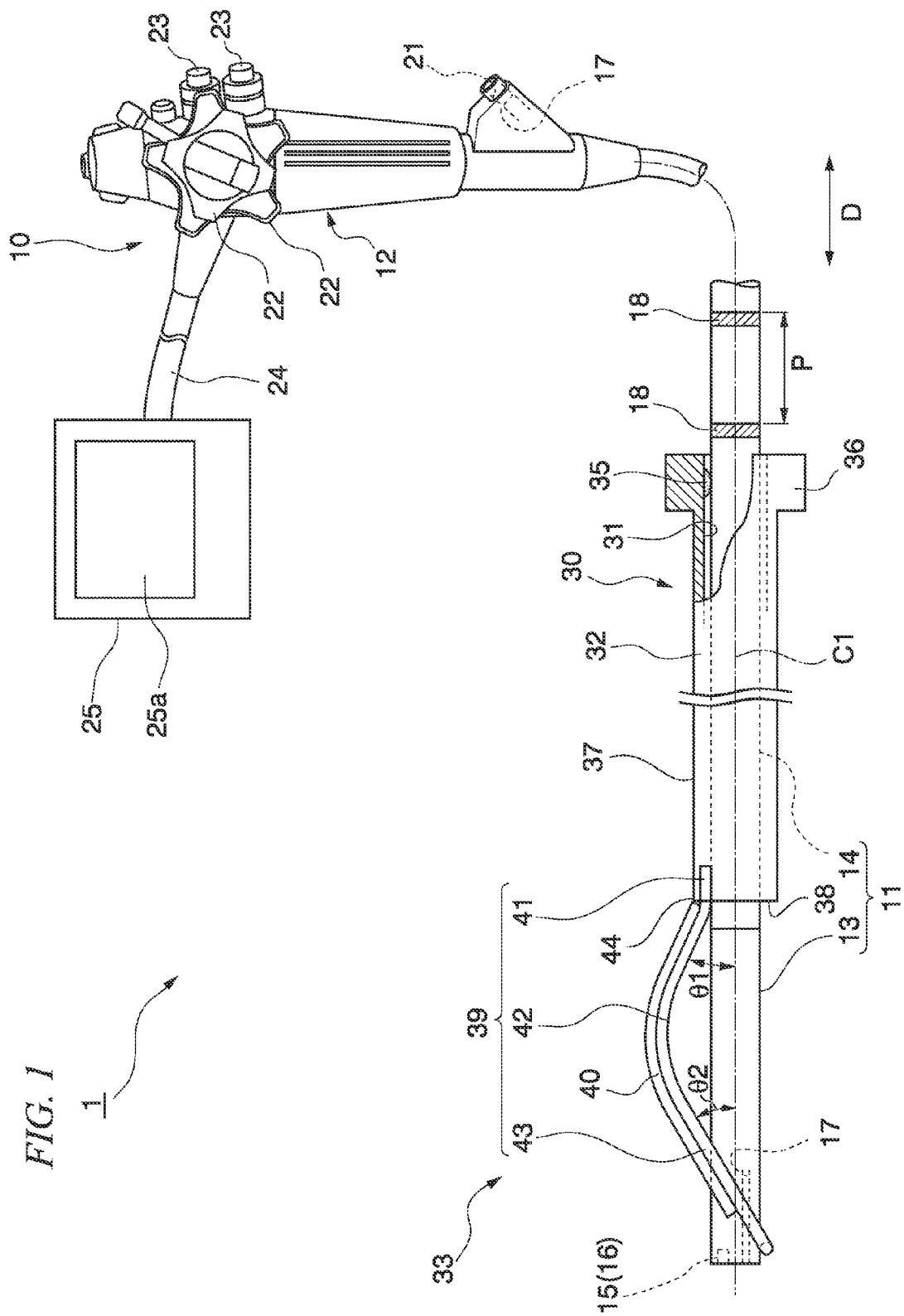
FIG. 1 is an overall view of an endoscope system of a first embodiment of the invention with a portion thereof being cut away.

As shown in FIG. 1, the endoscope system 1 of the present embodiment includes an endoscope 10 having a endoscope insertion part 11, that is long, and an overtube 30. The overtube 30 is an endoscope holding device having a lumen 31 that is an insertion passage into which the endoscope insertion part 11 is able to be inserted. In FIG. 1, the scales of some members are appropriately changed for convenience of description.

The endoscope 10 includes an endoscope insertion part 11, and an endoscope manipulating part 12 connected to the proximal end of the endoscope insertion part 11.

Figure 2:
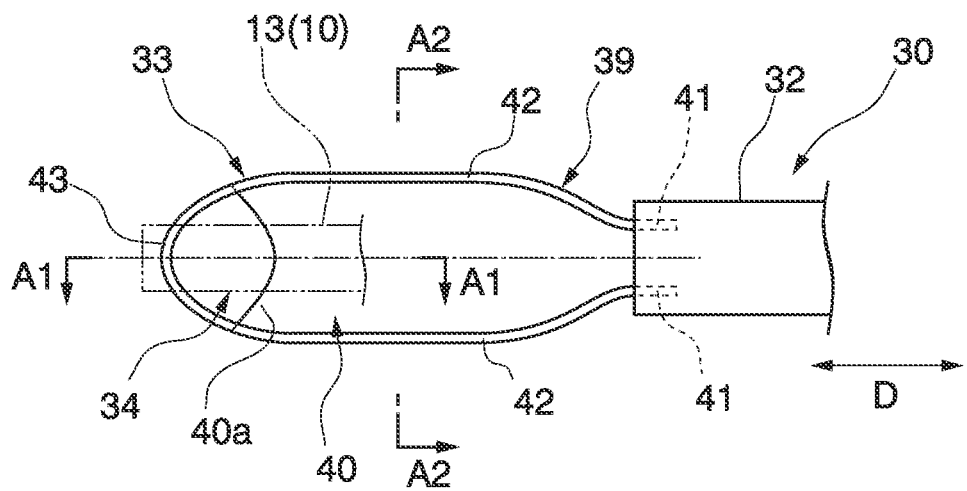
FIG. 2 is a bottom view of the distal end side of the endoscope system of FIG. 1.

As shown in FIGS. 1 and 2, the endoscope insertion part 11 has an endoscope curving portion 13 provided at the distal end and capable of being curved, and a long-axis member 14 connected to the proximal end of the endoscope curving portion 13. The long-axis member 14 may have flexibility, or may have such a degree of rigidity that a linear shape can be maintained in a non-loaded state.

A lighting unit 15 and an observation unit 16 are arranged at a distal end face of the endoscope curving portion 13, in a state where the lighting unit 15 and the observation unit 16 are exposed to the distal end side of the endoscope curving portion 13.

The lighting unit 15 has, for example, an LED, and can illuminate the front of the endoscope curving portion 13 by being supplied electric power from the endoscope manipulating part 12 side.

The observation unit 16 has an imaging element, such as a CCD. The observation unit 16 detects the light reflected by an observation object in front of the endoscope curving portion 13, and converts an image of the observation object into signals by photoelectric conversion.

An opening of a channel 17 is formed at the distal end face of the endoscope curving portion 13. The channel 17 extends to the endoscope manipulating part 12 through the endoscope curving portion 13 and the long-axis member 14.

The long-axis member 14 is provided with two scales (indexes) 18 for confirming the relative positions of the endoscope insertion part 11 and the overtube 30.

One of the scales 18 is provided at a position that satisfies the following conditions on the long-axis member 14. First, the endoscope insertion part 11 is inserted into the lumen 31 of the overtube 30. Then, the distal end face of the endoscope insertion part 11 and the distal end of a spatula part 33 are arranged to be at almost the same position in a longitudinal direction D. At this time, one of the scales 18 is provided at a position corresponding to a proximal end portion of the overtube 30 in the long-axis member 14.

The other of the scales 18 is provided at a position that satisfies the following conditions on the long-axis member 14. First, the endoscope insertion part 11 is inserted into the lumen 31 of the overtube 30. Then, the distal end face of the endoscope insertion part 11 and the distal end face of the insertion part 32 are arranged to be at almost the same position in the longitudinal direction D. At this time, the other of the scales 18 is provided at a position corresponding to the proximal end portion of the overtube 30 in the long-axis member 14.

The endoscope manipulating part 12 is provided with a forceps port 21 that is provided continuously with the channel 17 and leads to the channel 17. The endoscope manipulating part 12 includes switches 23. The manipulation of sending gas or liquid for curving the endoscope curving portion 13 is performed by one of the switches 23. The manipulation of suctioning the gas or liquid is performed by the other switch 23.

The endoscope manipulating part 12 is connected to devices, such as a power source and a monitor 25, via a universal cord 24. Thereby, an image detected by the observation unit 16 can be displayed on a screen 25a of the monitor 25.

As shown in FIG. 1, the overtube 30 includes the next configuration. The insertion part 32 with which the lumen 31 is formed. The spatula part (displacement part) 33 arranged at a fixing portion 44 of the distal end of the insertion part 32. A through hole (locking portion) 34 provided at the distal end of the spatula part 33. An airtight valve 35 provided inside the lumen 31.

The insertion part 32 has a long body portion 37, and holds the distal end of the endoscope 10 so as to freely protrude and retract. Additionally, the distal end of the insertion part 32 is provided with a distal end face 38 that specifies the protruding direction of the endoscope 10. In the present embodiment, the insertion part 32 is formed in a straight tubular shape as a whole and is formed of a hard metallic material compared to resin materials, for example, such as stainless steel. As an example, the internal diameter of the insertion part 32 is set to 17 mm, and the external diameter of the insertion part 32 is set to 19 mm. An outer peripheral surface of a proximal end portion of the insertion part 32 is provided with a cylindrical handle 36.

The airtight valve 35 provided inside the lumen 31 of the insertion part 32 is made from, for example, rubber, and contact air-tightly with an outer peripheral surface of the endoscope insertion part 11 inserted into the inside of the lumen 31.

The spatula part 33 displaces living body tissue in front of the insertion part 32 in order to secure the space for operating to curve the distal end part of the endoscope 10 protruded from the distal end face 38. The spatula part 33 has a displacement face curved toward the proximal end from the distal end and provided at a position apart from the distal end face 38.

The spatula part 33 is arranged such that the distal end side of the displacement face intersects a direction orthogonal to the distal end face 38, and is fixed to the insertion part 32 in the fixing portion 44. The arrangement of the spatula part 33 will be described below.

As shown in FIGS. 1 and 2, the spatula part 33 has a frame body 39 and a plate-like body 40. The frame body 39 is formed in an oval shape from plan view, and made from a material with a degree of hardness such that a linear shape can be maintained in a non-loaded state, such as a metal wire. The plate-like body 40 is provided so as to occlude a part of the space formed at the center of the frame body 39. In FIG. 2, for convenience of description, the endoscope curving portion 13 is shown by a two-dot chain line. In addition, when the frame body 39 is formed in the shape of a plate instead of a wire, the plate-like body 40 may be omitted.

The frame body 39 has a pair of proximal end portions 41 fixed to the insertion part 32, a pair of intermediate portions 42 that extend toward the distal end side from the proximal end portions 41, and a distal end portion 43 that is provided closer to the distal end than the intermediate portions 42 to connect the pair of intermediate portions 42 together. The pair of proximal end portions 41, the pair of intermediate portions 42, and the distal end portion 43 are integrally formed to constitute the frame body 39. As shown in FIG. 1, the frame body 39 is formed in the shape of an arch that is convex in a direction apart from a center axis C1 of the lumen 31 as seen from a side.

The pair of proximal end portions 41 of the frame body 39 is arranged on one side (on the upper side of the center axis C1 in FIG. 1) of the center axis C1 in a direction perpendicular to the center axis C1 as seen from the side. The pair of proximal end portions 41 is fixed to the insertion part 32, for example, by welding.

The intermediate portions 42 are arranged at positions farther from the center axis C1 than the proximal end portions 41 on one side of the center axis C1 at which the proximal end portions 41 are arranged. As shown in FIG. 1, the frame body 39 is formed such that a tangential line at the portion of the intermediate portion 42 at the proximal end side makes an angle $\theta 1$ that is an acute angle with respect to the center axis C1, as seen from the side. In the present embodiment, the angle $\theta 1$ is set to about 20°.

As shown in FIG. 1, the distal end portion 43 of the frame body 39 is arranged at a position closer to the center axis C1 than the position of the distal end of the intermediate portion 42, or a position opposite to the center axis C1 across the center axis C1, as seen from the side. As shown in FIG. 1, the frame body 39 is formed such that a tangential line at the distal end portion 43 makes an angle $\theta 2$ that is an acute angle with respect to the center axis C1, as seen from the side. In the present embodiment, the angle θ2 is set to about 30°.

The angle θ1 is not limited to 20°, and the angle θ2 is not limited to 30°. The angle θ1 and the angle θ2 can be appropriately set in consideration of the manipulability or the like of the spatula part 33. In addition, the angle θ1 and the angle θ2 may be the same.

The plate-like body 40 is made from a transparent resin material having light permeability, such as an acrylic. A cutout portion 40a that is cut out substantially in a U-shape is formed at a distal end of the plate-like body 40. The aforementioned through hole 34 is formed by the distal end portion 43 of the frame body 39 and the cutout portion 40a of the plate-like body 40. The plate-like body 40 extends to a width equivalent to the width of the frame body 39 in the width direction. The portion of the plate-like body 40 at the proximal end side in the longitudinal direction extends to the vicinity of the proximal end portion 41 of the frame body 39.

Figure 3:
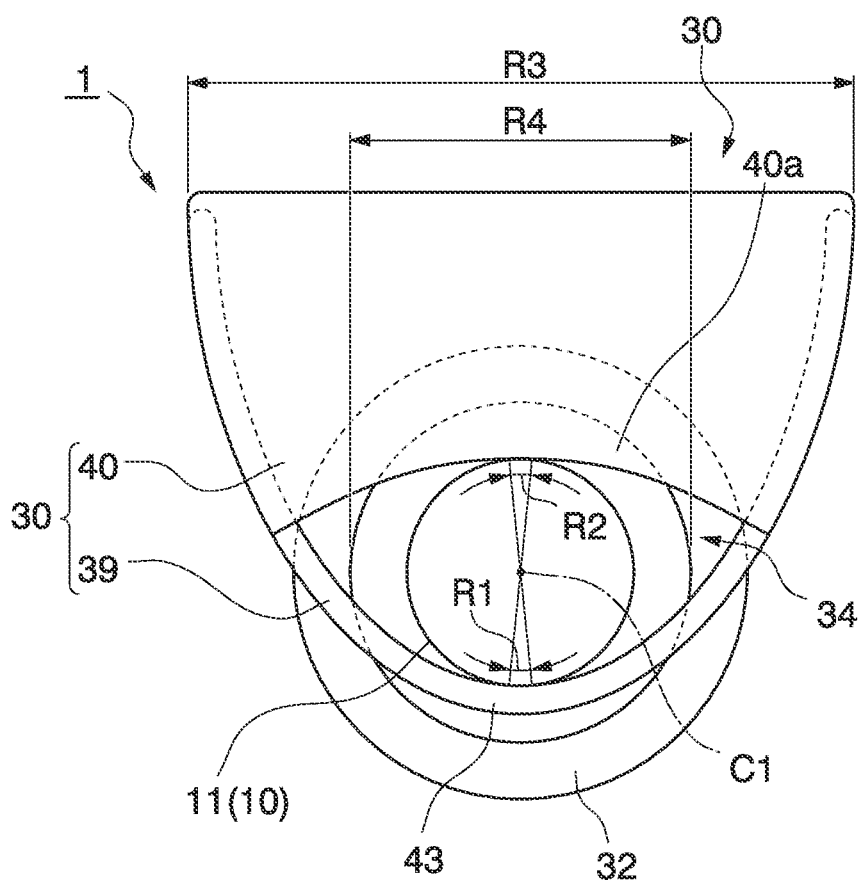
FIG. 3 is a front view of the distal end side of the endoscope system of FIG. 1.

The through hole 34 is provided on the center axis C1 of the lumen 31. The through hole 34 is arranged at a position apart by a predetermined distance forward (toward the distal end side) from an opening portion of the lumen 31. As shown in FIG. 3, the internal diameter of the through hole 34 is formed with a size that the endoscope insertion part 11 is able to be inserted into the hole. Furthermore, the internal diameter of the through hole 34 is formed at a position and with a size such that the endoscope insertion part 11 is able to be inserted into the hole while sliding ranges R1 and R2 around outer peripheral surface of insertion part 11 to an inner surface of the through hole 34.

That is, in a cross-section of the endoscope insertion part 11 and the insertion part 32 shown in FIG. 3, the through hole 34 is formed such that the diameter of an inscribed circle satisfies the following first and second conditions. The first condition is that the portion of the endoscope insertion part 11 within the predetermined range R1 in the circumferential direction comes into contact with the inside of the distal end portion 43 of the frame body 39, when the endoscope insertion part 11 is passed through the through hole 34. The second condition is that the portion of the endoscope insertion part 11 within the predetermined range R2 in the circumferential direction comes into contact with the cutout portion 40a of the plate-like body 40, when the endoscope insertion part 11 is passed through the through hole 34.

The distance in the vertical direction (direction perpendicular to the center axis C1 and perpendicular to the width direction of the spatula part 33) in FIG. 3 between the distal end portion 43 of the frame body 39 and the cutout portion 40a of the plate-like body 40 is set to be equal to or slightly larger than the external diameter of the endoscope insertion part 11. In the endoscope insertion part 11, the region R1 that is a portion that touches the cutout portion 40a, and the region R2 that is a portion that touches the distal end portion 43 are set so as to be in positions that are almost symmetrical with respect to the center axis C1.

Figure 4:
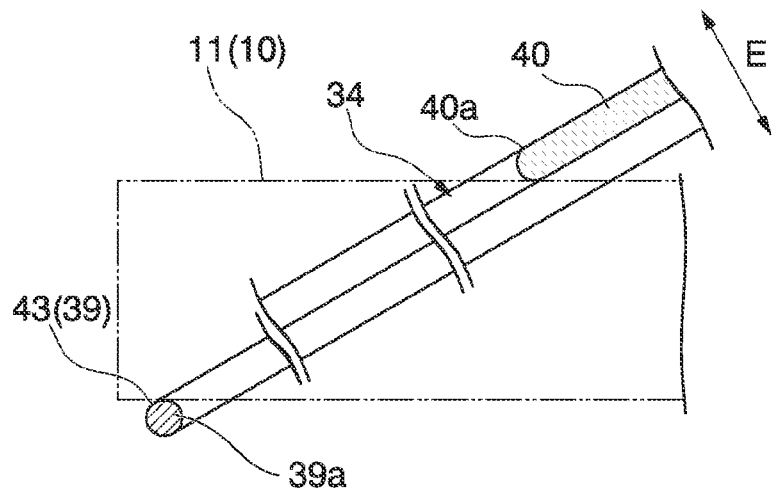
FIG. 4 is a cross-sectional view taken along a cutting line A1 to A1 in FIG. 2.

As shown in FIG. 4, an edge 39a of the distal end portion 43 of the frame body 39 at the through hole 34 is formed in a shape having a convex curved surface that protrudes toward the through hole 34 side in a direction perpendicular to the thickness direction E of the plate-like body 40. Furthermore, an edge of the cutout portion 40a of the plate-like body 40 is formed in a shape having a convex curved surface that protrudes toward the through hole 34 in a direction perpendicular to the thickness direction E of the plate-like body 40. More specifically, the curvature radius of an outer peripheral surface of the edge 39a of the distal end portion 43 is formed so as to be equal to or larger than a predetermined value. The predetermined value of the curvature radius in the present embodiment is, for example, 2 mm. In addition, the frame body 39 may be formed from a wire with a circular cross-section, and the radius of the circular cross-section may be equal to or more than the aforementioned predetermined curvature radius.

The edge of the cutout portion 40a of the plate-like body 40 protrudes in the shape of an arch toward the through hole 34. A curve that constitutes an end face of the cutout portion 40a is also formed to have the aforementioned predetermined curvature radius (2 mm) or more.

In this way, the through hole 34 is provided so as to be able to lock the distal end part of the endoscope insertion part 11.

Figure 5:
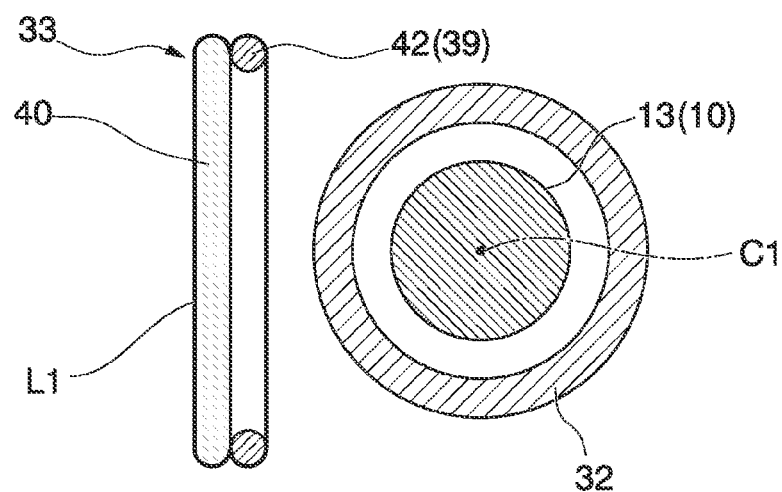
FIG. 5 is a cross-sectional view taken along a cutting line A2 to A2 in FIG. 2.

As shown in FIG. 2, as seen from a direction orthogonal to the center axis C1 of the lumen 31 and orthogonal to the width direction of the spatula part 33, the outer peripheries of the frame body 39 and the plate-like body 40 are formed to have the aforementioned predetermined curvature radius or more. Moreover, as shown in FIG. 5, the outer periphery L1 of a cross-section of the spatula part 33 in a plane orthogonal to the longitudinal direction D of the insertion part 32 is formed to have a predetermined curvature radius or more in any portion.

As shown in FIG. 3, as seen from a direction parallel to the center axis C1 of the lumen 31, a range R3 occupied by the plate-like body 40 includes a range R4 occupied by the inner cavity of the insertion part 32 in the width direction of the plate-like body 40. Furthermore, the length of the outer periphery L1 of the spatula part 33 is set to be equal to or less than the length of the outer periphery of the insertion part 32. Since the insertion part 32 is formed in a tubular shape in the present embodiment, the length of the outer periphery L1 is set to about 3.14 times or less the diameter of the insertion part 32.

Figure 6:
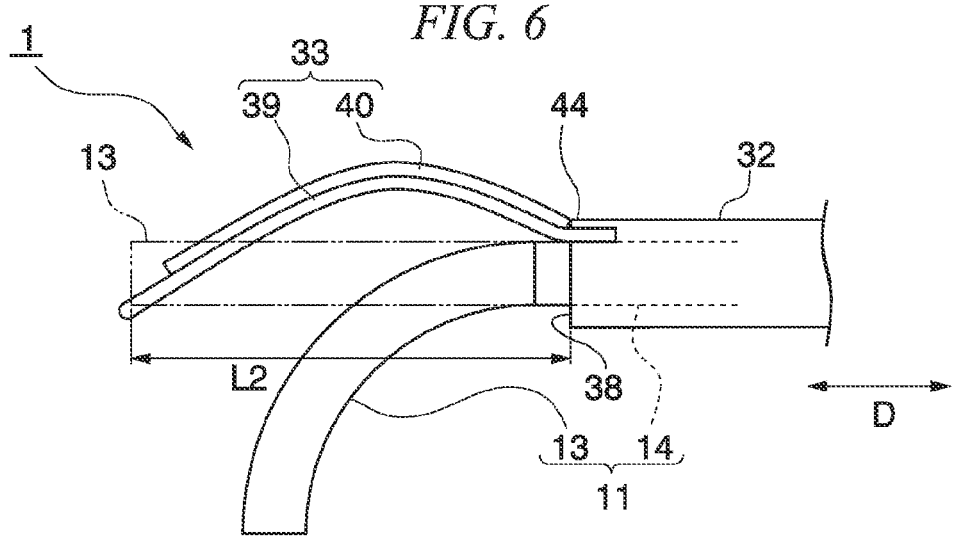
FIG. 6 is a side view illustrating a state where an endoscope curving portion of the endoscope system of FIG. 1 is curved.

Moreover, as shown in FIG. 6, the spatula part 33 is configured such that the length of the portion of the spatula part 33 in front of the distal end face of the insertion part 32 becomes equal to or more than the length L2 of the endoscope curving portion 13 in the longitudinal direction D. In the present embodiment, the length of the portion of the spatula part 33 in front of the distal end face of the insertion part 32 is set to, for example, about 120 mm.

Next, a procedure of inserting the endoscope system 1 from the rectum to perform the treatment of the stomach will be described as an example of a Natural Orifice Translumenal procedure using the endoscope system 1 configured as described above. Furthermore, the following procedure is performed on a patient lying on his back.

First, an operator inserts the endoscope insertion part 11 into the rectum through a patient's anus. At this time, the operator makes the front of the endoscope curving portion 13 irradiated with light from the lighting unit 15, and inserts the endoscope insertion part 11 while observing an image detected by the observation unit 16 on the screen 25a of the monitor 25.

Figure 7:
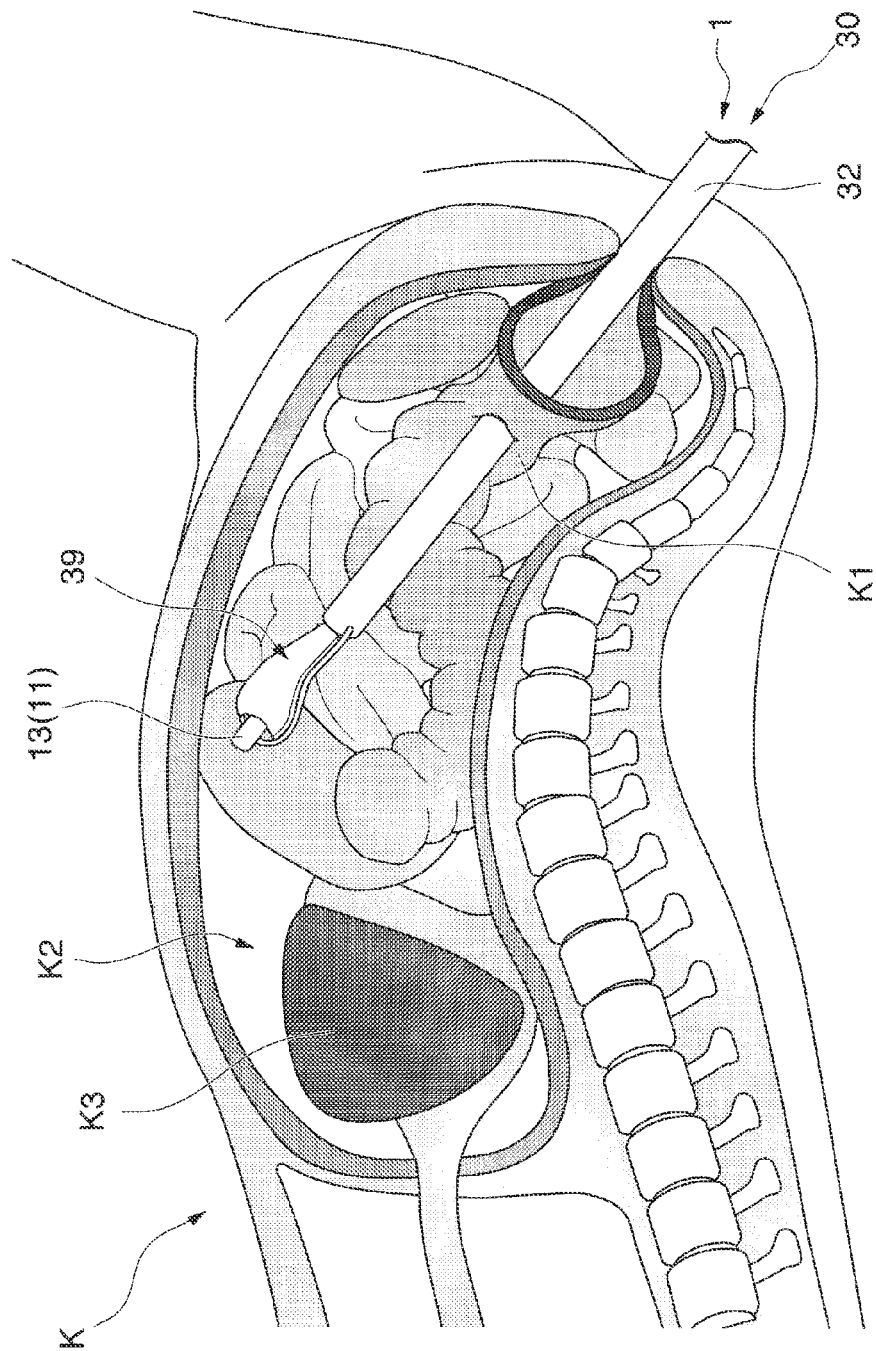
FIG. 7 is a longitudinal cross-sectional view explaining a procedure using the endoscope system of FIG. 1.

Then, as shown in FIG. 7, the endoscope is made to pass through an abdominal cavity from the intestinal wall at a position where the endoscope is inserted into from the anus with a predetermined distance. Since the position where the endoscope is inserted into from the anus with a predetermined distance is a position where the intestinal wall is the front of the anus, the endoscope is easy to approach. Additionally, at the above position, the endoscope can reach the abdominal cavity if the endoscope passes through the intestinal wall.

For example, a high-frequency knife is inserted into the channel 17 of the endoscope 10 as a method of passing through the intestinal wall. Then, a incision is formed in the intestinal wall by the high-frequency knife, and a balloon catheter passed through the channel 17 is inserted into the incision. Thereafter, the incision is widened for endoscope to pass through by inflating the balloon. Then, in that state, the endoscope 10 is pushed into the incision and is made to access the abdominal cavity.

Next, the endoscope insertion part 11 is pulled out from the rectum, and the balloon catheter is taken out from the channel 17. At this time, the position of the incision may be held by a guide wire or the like. Then, the endoscope insertion part 11 is inserted into the lumen 31 of the overtube 30 outside a patient's body.

Further, the endoscope insertion part 11 is made to protrude to the front of the insertion part 32 of the overtube 30, and the distal end part of the endoscope insertion part 11 is inserted into the through hole 34 of the spatula part 33 and is locked. Along with this, the distal end of the spatula part 33 and the distal end face of the endoscope insertion part 11 are adjusted so as to be at almost the same position in the longitudinal direction D.

The endoscope insertion part 11 is passed through the through hole 34 in a state where the regions R1 and R2 of the outer peripheral surface thereof are brought into contact with the edge of the through hole 34. Therefore, the endoscope insertion part 11 is prevented from slipping out unintentionally from the through hole 34. Additionally, the position of the endoscope insertion part 11 in the longitudinal direction D with respect to the overtube 30 is gently fixed by the friction between the airtight valve 35 inside the lumen 31 of the insertion part 32 and the endoscope insertion part 11.

At this time, the relative position of the endoscope 10 in the longitudinal direction D with respect to the overtube 30 is confirmed by confirming the positional relationship between the proximal end portion of the overtube 30 and the scales 18.

As shown in FIG. 7, the endoscope insertion part 11 to which the overtube 30 is attached is inserted into an abdominal cavity K2 from the incision of the rectum K1 in a state where the endoscope insertion part 11 is guided by the guide wire. Then, the abdominal cavity K2 is insufflated by allowing gas to flow thereinto through the channel 17 of the endoscope 10, the lumen 31 of the overtube 30, or the like.

Figure 8:
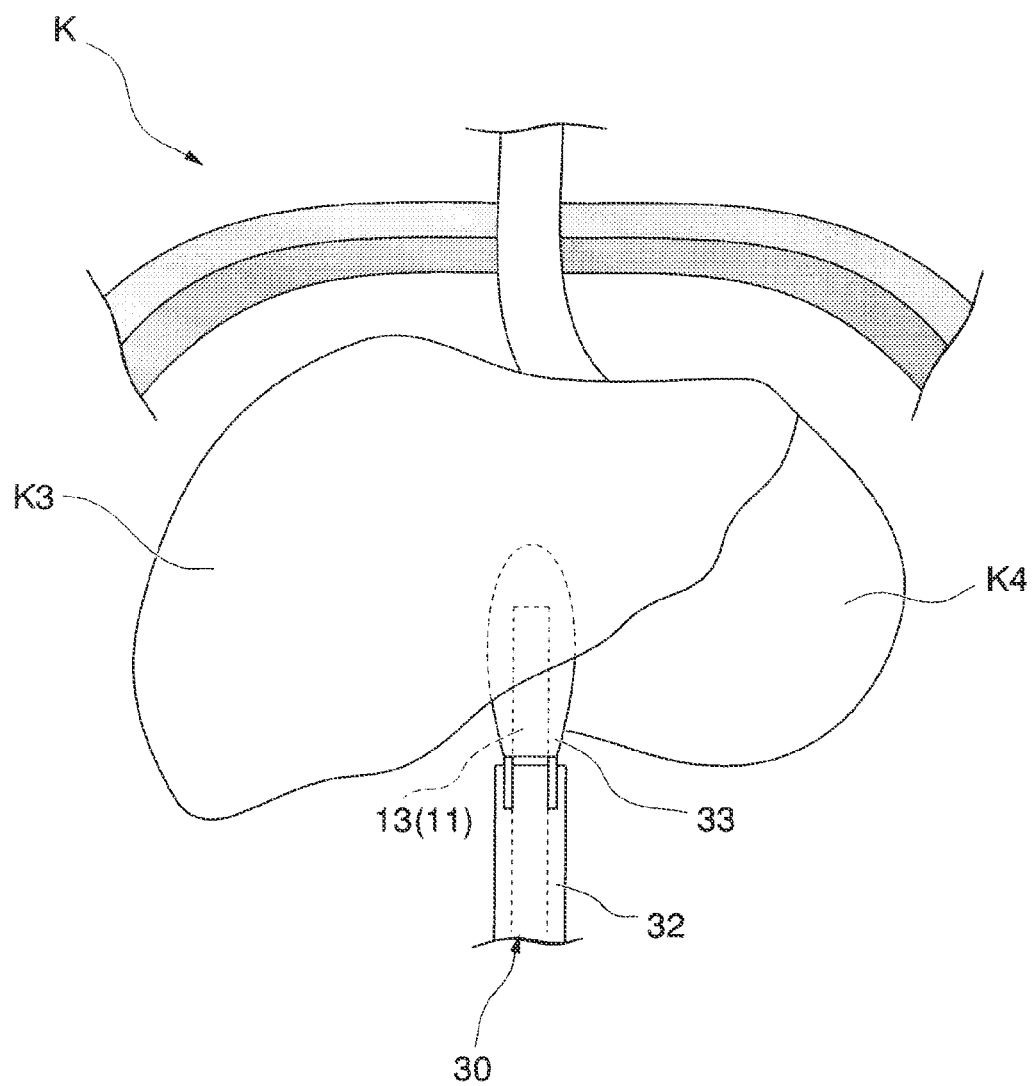
FIG. 8 is a transverse cross-sectional view of essential parts explaining a procedure using the endoscope system of FIG. 1.

The operator inserts the spatula part 33 under an internal organ, such as the liver K3 to be displaced, as shown in FIG. 8, in a state where the distal end part of the endoscope insertion part 11 is locked to the through hole 34 of the overtube 30, while observing the screen 25a. Thereafter, the liver K3 is lifted up and displaced by the spatula part 33, and space is secured below the spatula part 33 and between the liver K3 and the stomach K4.

While performing the operation from the passing through to the displacement, the operator confirms that the position of the overtube 30 in the longitudinal direction D with respect to the endoscope insertion part 11 is maintained depending on the position of the scales 18 with respect to the proximal end portion of the overtube 30.

Next, the endoscope insertion part 11 is pulled in a predetermined length with respect to the overtube 30. By pulling as described above, the distal end part of the endoscope insertion part 11 is removed from the through hole 34 of the spatula part 33 and causes the endoscope insertion part 11 to be independently moved with respect to the spatula part 33.

Figure 9:
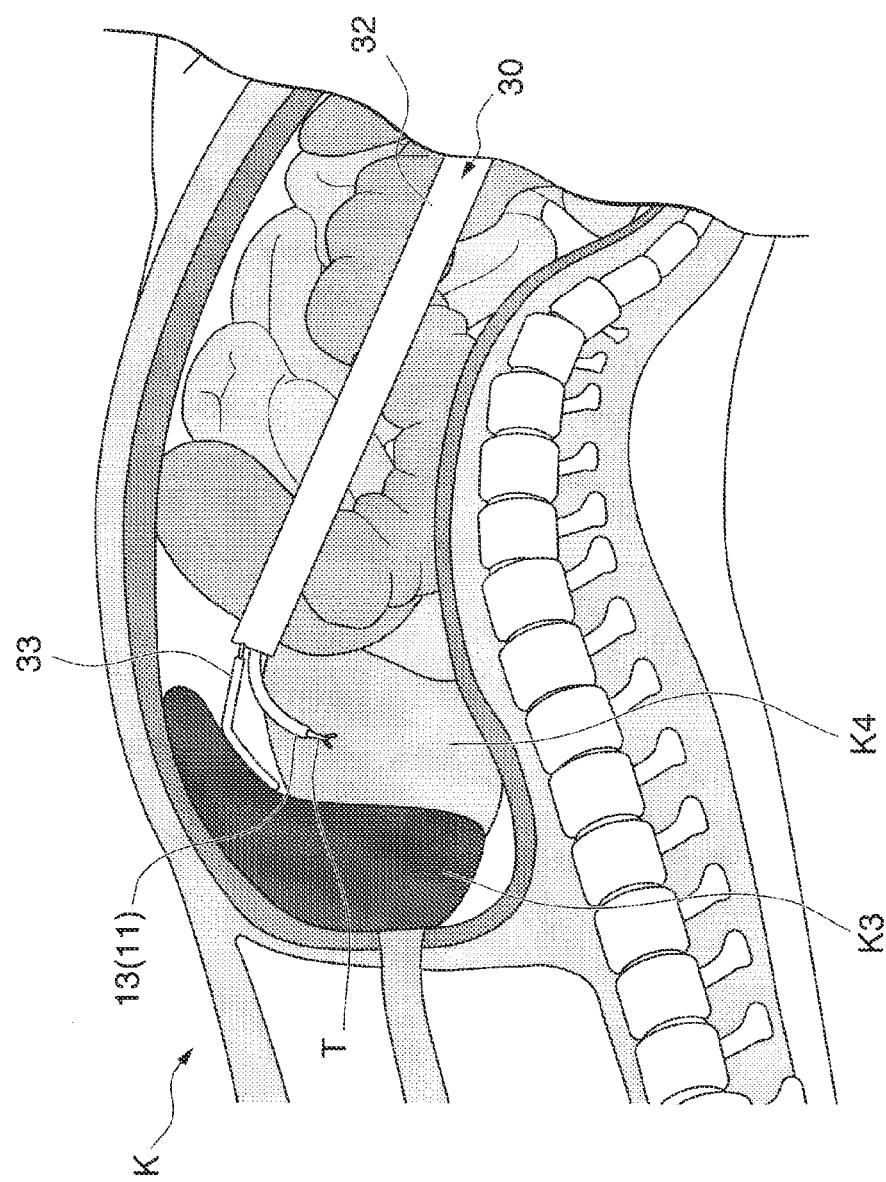
FIG. 9 is a longitudinal cross-sectional view of essential parts explaining a procedure using the endoscope system of FIG. 1.

Moreover, as shown in FIG. 9, a treatment part, such as a front wall of the stomach K4, is approached by manipulating the knob 22 of the endoscope manipulating part 12 to curve the endoscope curving portion 13 downward while supporting the liver K3 with the spatula part 33. Thereby, the endoscope 10 can be freely moved within the space made under the spatula part 33, and a good operative field around the target to be treated is obtained.

Figure 10:
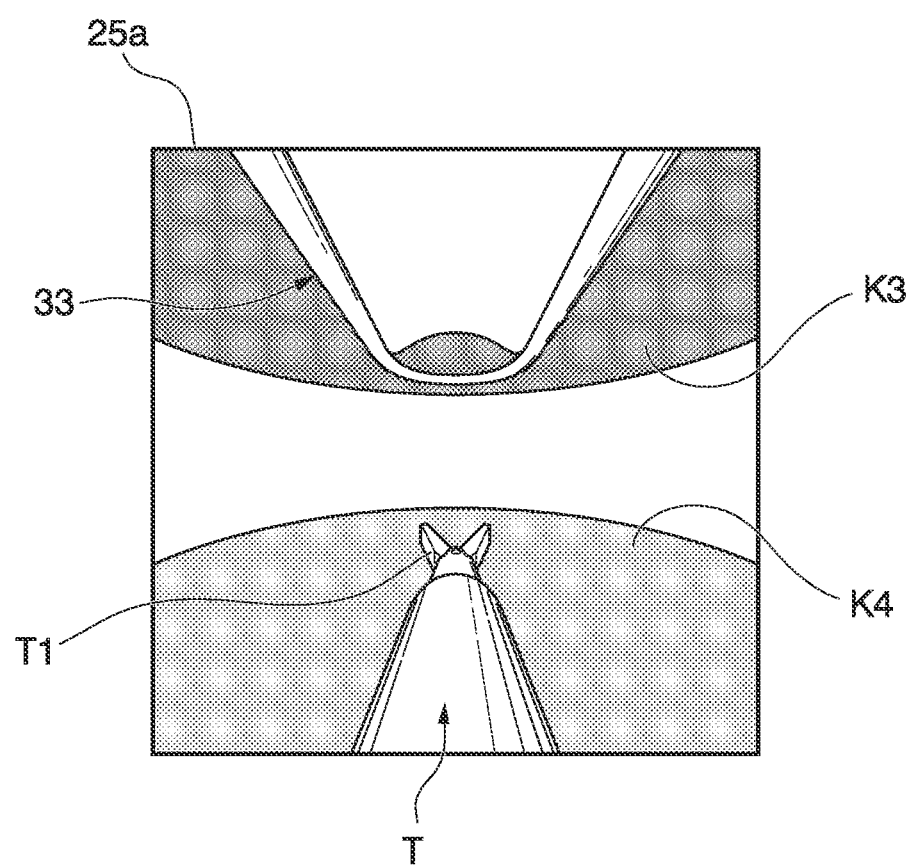
FIG. 10 is a diagram explaining an image displayed on a screen of a monitor in a procedure using the endoscope system of FIG. 1.

Here, grip forceps T (refer to FIG. 9) or the like are inserted into the channel 17 of an endoscope 10, and are made to protrude from the distal end of the endoscope insertion part 11. Then, as shown in FIG. 10, a treatment part T1 between the spatula part 33 that supports the liver K3 and the stomach K4 can be confirmed on the screen 25a of the monitor 25. Procedures, such as the Heller-Dor method, are performed on the front wall of the stomach K4 and the esophagus, using the grip forceps T, a high-frequency knife, or the like.

In addition, for example, the procedures are performed according to the following sequence when the endoscope insertion part 11 to which the overtube 30 is attached is moved to another part within the abdominal cavity K2 of the patient K.

First, while observing the screen 25a, the operator manipulates the knob 22 of the endoscope manipulating part 12 to extend the endoscope curving portion 13 straight, and pulls the endoscope insertion part 11 by a predetermined length with respect to the overtube 30.

Then, the endoscope insertion part 11 is pushed into the overtube 30 while adjusting the curving state of the endoscope curving portion 13. Then, the distal end part of the endoscope insertion part 11 is inserted into and locked to the through hole 34 of the spatula part 33, and the overtube 30 and the endoscope insertion part 11 are integrated with each other again.

At this time, the relative position of the endoscope 10 in the longitudinal direction D with respect to the overtube 30 is confirmed by confirming the positional relationship between the proximal end portion of the overtube 30 and the scales 18.

Then, the endoscope insertion part 11, to which the overtube 30 is attached, is moved to a desired part. When a treatment is performed, the distal end part of the endoscope insertion part 11 is removed from the through hole 34 of the spatula part 33 and the endoscope insertion part 11 is independently moved with respect to the spatula part 33.

In the endoscope system 1 of the present embodiment, the through hole 34 is provided in the overtube 30. Therefore, the overtube 30 and the endoscope insertion part 11 are compactly integrated with each other by locking the distal end part of the endoscope insertion part 11 to the through hole 34. For this reason, it is possible to reduce that the endoscope insertion part 11 to which the overtube 30 is attached hits surrounding an internal organs or the like within the abdominal cavity K2 of the patient K, to easily move the endoscope insertion part 11.

Furthermore, when the endoscope insertion part 11 to which the overtube 30 is attached is inserted into an abdominal cavity, the insertion cannot be performed under direct vision but may be performed only in the visual field of the endoscope. Even in this case, both the overtube 30 and the endoscope insertion part 11 can be reliably inserted from one incision provided in the endoscope. Therefore, the burden imposed on the patient K can be reduced.

Since the through hole 34 formed at the distal end of the spatula part 33 is provided as the locking portion, the distal end part of the endoscope insertion part 11 can be reliably locked.

Since the through hole 34 is formed with a size such that the endoscope insertion part 11 is inserted thereinto, the endoscope insertion part 11 can be easily inserted into the through hole 34.

Moreover, since the through hole 34 is provided on the center axis C1 of the lumen 31, the endoscope insertion part 11 can be simply inserted into the through hole 34 just by pushing out the endoscope insertion part 11 inserted into the lumen 31 straightforwardly.

The through hole 34 of the overtube 30 is formed at a position and with a size such that the endoscope insertion part 11 can be passed through, in a state where the regions R1 and R2 of the outer peripheral surface of the endoscope insertion part 11 are brought into contact with the edge of the through hole 34. For this reason, it is possible to prevent the position of the endoscope insertion part 11 from deviating in the radial direction or in the longitudinal direction within the through hole 34, to reliably lock the endoscope insertion part 11.

The edge of the through hole 34 in the spatula part 33 is formed in a shape having a convex curved surface in a direction perpendicular to the thickness direction E of the edge. Therefore, when the endoscope insertion part 11 is inserted into the through hole 34, it is possible to prevent the outer peripheral surface of the endoscope insertion part 11 from being damaged.

Additionally, the overall insertion part 32 is formed from a material with a degree of hardness such that the linear shape can be maintained in a non-loaded state. Therefore, a force applied to the proximal end of the insertion part 32 can be reliably transmitted toward the distal end to reliably perform exclusion. Additionally, since the operator can directly feel a force applied to the distal end, the endoscope can be safely used without applying such a degree of force that an internal organ is damaged.

Since the spatula part 33 has the frame body 39 formed from a metallic material that is hard as compared to a resin material, an internal organ or the like can be reliably supported on the frame body 39.

Moreover, the spatula part 33 has the plate-like body 40 that occludes a part of the space formed at the center of the frame body 39. Therefore, it is possible to prevent an internal organ supported on the frame body 39 or the like from hang down or falling downward from a region inside the frame body 39. Furthermore, since a force applied to an internal organ is dispersed over a wide area, it can be displaced while protecting the internal organ.

The plate-like body 40 is made from a material having light permeability. Therefore, a position where is the opposite side across the plate-like body 40 from an observation position by using the observation unit 16 can be confirmed through the plate-like body.

The plate-like body 40 is formed so that the range R3 occupied by the plate-like body 40 include the range R4 occupied by the inner cavity of the insertion part 32, in the width direction of the plate-like body 40 as seen from a direction parallel to the center axis C1 of the lumen 31 and perpendicular to the width direction of the plate-like body 40. In this way, the plate-like body 40 is formed with as large a width as possible. For this reason, an internal organ or the like can be reliably displaced from a range through which the endoscope insertion part 11 passes, in the width direction of the plate-like body 40.

Also, the length of the outer periphery of the spatula part 33 in a cross-section orthogonal to the longitudinal direction D of the insertion part 32 of the spatula part 33 is set to be equal to or less than the length of the outer periphery of the insertion part 32. Accordingly, when the overtube 30 passes through an incision formed in a rectum wall, a stomach wall, or the like, it is possible to prevent the incision from being expanded so that the length around the incision becomes larger than the length of the outer periphery of the insertion part 32, and to reduce the burden imposed on the patient K.

The intermediate portions 42 of the spatula part 33 is arranged at a position farther from the center axis C1 of the lumen 31 than the proximal end portions 41 in the longitudinal direction D. For this reason, an operative field can be more widely secured between the intermediate portions 42 and the center axis C1.

Moreover, as seen from the direction orthogonal to the longitudinal direction D, the distal end portion 43 of the frame body 39 is arranged closer to the center axis C1 than the distal end side of the intermediate portions 42 or on the opposite side beyond the center axis C1. Accordingly, it is possible to provide the through hole 34 is provided at the distal end of the spatula part 33 almost on the center axis C1, and to easily insert the endoscope insertion part 11 into the through hole 34.

The spatula part 33 is formed such that the outer periphery thereof has a predetermined curvature radius or more in bottom view, and is formed such that the outer periphery of a cross-section in a plane orthogonal to the longitudinal direction D has the predetermined curvature radius or more. Thereby, for example, when the spatula part 33 is inserted into a gap between internal organs, such as the liver, it is possible to prevent tissues from being damaged or bleeding and to prevent the main operation from being interrupted.

Furthermore, the spatula part 33 is configured such that the length of a portion in front of the distal end face of the insertion part 32 becomes equal to or more than the length L2 of a portion in front of the distal end face of the insertion part 32 of the endoscope curving portion 13. Therefore, when the endoscope curving portion 13 is curved in the longitudinal direction D, a sufficient treatment can be performed in the secured space where an internal organ is displaced by the spatula part 33.

Since the scales 18 are provided on the endoscope insertion part 11 in the longitudinal direction D, the length of the endoscope insertion part 11 inserted into the lumen 31 of the overtube 30 can be easily recognized outside a body.

In the present embodiment, the through hole 34 that is the locking portion is configured by occlating a part of the space, which is formed at the center of the frame body 39 formed in an oval shape, by the plate-like body 40 in the spatula part 33. However, the spatula part and the locking portion can adopt various configurations as shown below.

Figure 11:
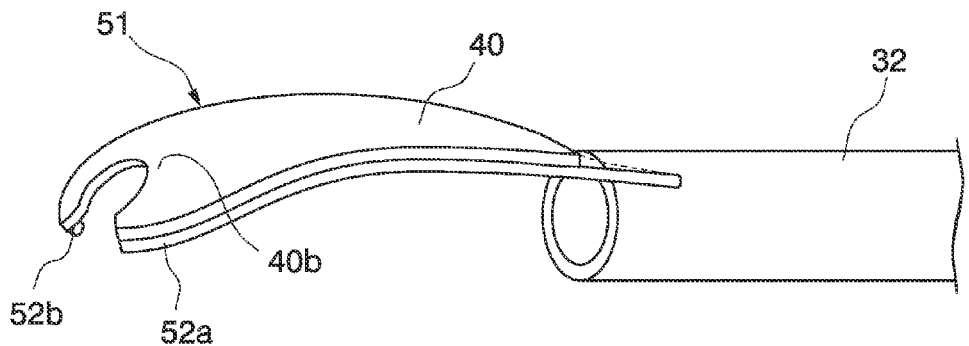
FIG. 11 is a perspective view of essential parts of an endoscope holding device in a modification of the first embodiment of the invention.

For example, the spatula part 51 shown in FIG. 11 has a pair of frame bodies 52a and 52b in a shape in which an oval frame body 39 is cut at a fold-back portion at the distal end, instead of the frame body 39 formed in an oval shape in the spatula part 33 of the present embodiment.

The cutout portion 40b, which is formed substantially in a C-shape, that the endoscope insertion part 11 can be locked, is formed at the distal end of the plate-like body 40, and the cutout portion 40b constitutes the locking portion in the present modification.

Figure 12:
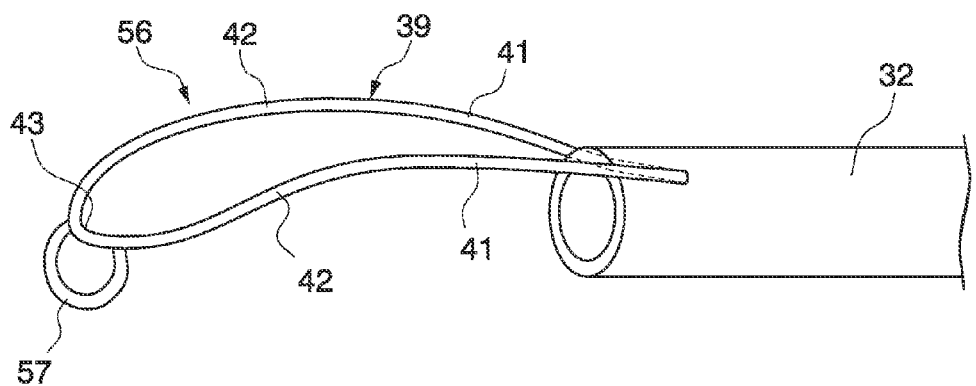
FIG. 12 is a perspective view of essential parts of an endoscope holding device in a modification of the first embodiment of the invention.

The spatula part 56 shown in FIG. 12 has a locking member 57 arranged inside the frame body 39 which is formed substantially in a C-shape and is formed of a hard material, such as a wire, and is formed in the shape of an arch as seen from the side, instead of the through hole 34 provided in the plate-like body 40 of the spatula part 33 of the present embodiment.

The locking member 57 is connected to the frame body 39 by welding or the like. In the present modification, the locking member 57 and the distal end portion 43 constitute the locking portion.

Figure 13:
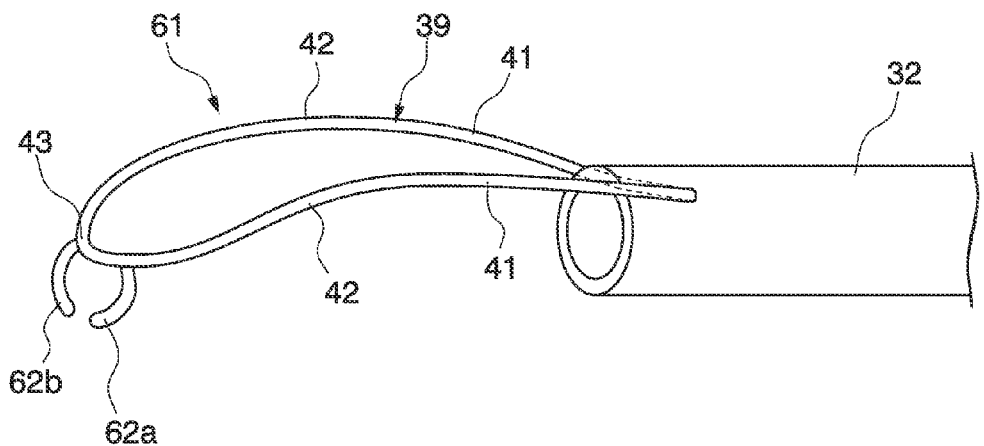
FIG. 13 is a perspective view of essential parts of an endoscope holding device in a modification of the first embodiment of the invention.

Furthermore, the spatula part 61 shown in FIG. 13 has a pair of locking members 62a and 62b in a shape in which a substantially C-shaped locking member 57 is cut at a fold-back portion, instead of the locking member 57 of the spatular part 56 of the above modification. In the present modification, the locking members 62a and 62b and the distal end portion 43 constitute the locking portion.

Furthermore, in the spatula part 56 and the spatula part 61, the plate-like body may be arranged so as to occlate a part or the whole of the space formed at the center of the frame body 39.

Moreover, the overall spatula part may be made from a metallic plate.

In the present embodiment, the through hole 34 of the overtube 30 is provided on the center axis C1 of the lumen 31. However, the endoscope insertion part inserted into the lumen 31 of the overtube 30 may have the endoscope curving portion. In such a case, since the endoscope curving portion is curved, the endoscope insertion part is able to be inserted into the through hole irrespective of the position of the through hole. For this reason, the through hole may not be provided on the center axis C1. As long as the through hole can lock the endoscope insertion part, the through hole may be formed so as to be sufficiently large with respect to the external diameter of the endoscope insertion part.

Additionally, in the present embodiment, the intermediate portions 42 are arranged at a position farther from the center axis C1 than the proximal end portions 41. However, this configuration is not essential. For example, when the size of the operative field is satisfactory, the intermediate portions may be formed so as to extend forward parallel to the center axis C1 such that the distance from the center axis C1 does not change the distance from the center axis C1 at the proximal end portion. Similarly, the distal end portion may be formed so as to extend forward parallel to the center axis C1 such that the distance from the center axis C1 does not change the distance from the center axis C1 at the intermediate portions.

In the present embodiment, the whole of the insertion part 32 of the overtube 30 is formed straight and made from a hard material. However, at least a portion of the insertion part may be curved. Furthermore, in case that the whole of the endoscope insertion part is made from a hard material, the insertion part 32 of the overtube 30 may be made from an elastic material, such as resin.

In the present embodiment, the operator integrates and manipulates the overtube 30 and the endoscope insertion part 11 by himself. However, a well-known advance and retreat lock mechanism that can fix and release the position of the endoscope insertion part 11 inserted into the lumen 31 may be provided within the handle 36.

The procedure using the above endoscope system 1 adopts the sequence of lifting up the liver K3 with the spatula part 33 in a state where the distal end part of the endoscope insertion part 11 is locked to the through hole 34 of the overtube 30, and then removing the distal end part of the endoscope insertion part 11 from the through hole 34. Instead of this sequence, a sequence of removing the distal end part of the endoscope insertion part 11 from the through hole 34 of the overtube 30 and then lifting up the liver K3 with the spatula part 33 may be adopted.

Furthermore, a treatment may be performed in an operative field secured above the spatula part 33 while displacing an internal organ downward with the spatula part 33, and a treatment may be performed in an operative field secured in the part adjacent to the spatula part 33 while displacing an internal organ laterally with the spatula part 33. Moreover, a treatment may be performed after an internal organ is displaced in any direction with the spatula part 33.

Second Embodiment

Next, although a second embodiment according to the invention will be described with reference to FIG. 14, the description of the same parts as the above embodiment will be omitted by giving the same reference numerals thereto, and only different points will be described.

Figure 14:
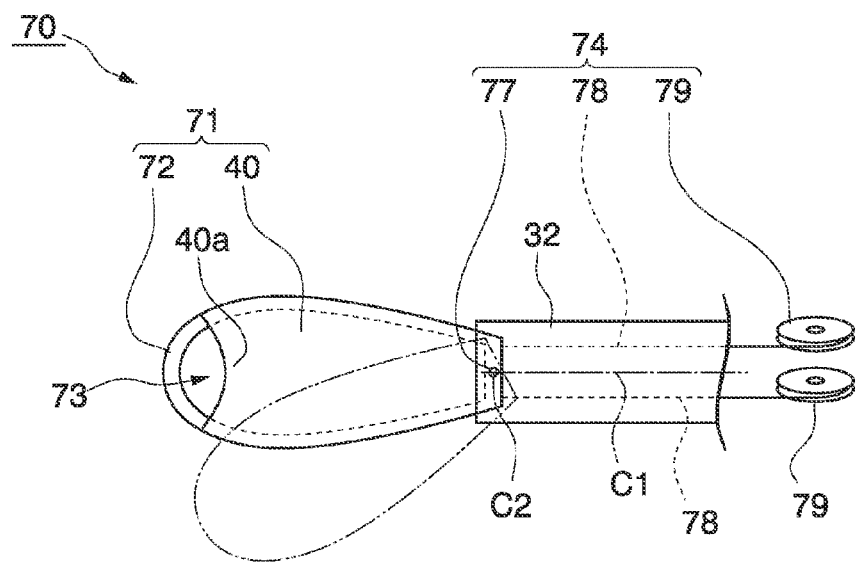
FIG. 14 is a plan view of essential parts of an endoscope holding device of a second embodiment of the invention.

As shown in FIG. 14, an endoscope system of the present embodiment includes an overtube 70 that is the endoscope holding device, instead of the overtube 30 of the endoscope system 1 of the first embodiment. The overtube 70 has a spatula part 71 that is configured so as to be able to rotate around an axis C2 orthogonal to the center axis C1 of the lumen 31, instead of the spatula part 33 of the overtube 30.

The spatula part 71 has a frame body 72 formed substantially annularly and made from a hard material, such as a wire, and the plate-like body 40 that occlates a part of the space formed at the center of the frame body 72. A through hole 73 is formed by the distal end of the frame body 72 and the cutout portion 40a of the plate-like body 40.

The spatula part 71 is connected to a rotating mechanism 74 that rotatably supports a proximal end portion of the frame body 72 in the distal end portion of the insertion part 32.

The rotating mechanism 74 has a pivoting member 77 attached to the distal end portion of the insertion part 32 and rotatably supports the frame body 72 around the axis C2, a pair of manipulation wires 78 connected to a proximal end portion of the frame body 72 such that their respective distal ends sandwich the pivoting member 77, and pulleys 79 connected to proximal ends side of the manipulation wires 78, respectively.

A ratchet mechanism (not shown) is connected to each pulley 79. The ratchet mechanism holds the pulley 79 in a state where the manipulation wire 78 is pulled by a predetermined length. The ratchet mechanisms can release the holding of the pulleys 79.

According to the endoscope system of the present embodiment configured in this way, the overtube 70 and the endoscope insertion part 11 can be compactly integrated with each other.

Moreover, since the spatula part 71 is configured to be rotatable around the axis C2, the orientation of the spatula part 71 with respect to the center axis C1 of the lumen 31 in planar view can be arbitrarily changed, and the approach property of the spatula part 33 can be improved.

Third Embodiment

Next, although a third embodiment according to the invention will be described with reference to FIG. 15, the description of the same parts as the above embodiment will be omitted by giving the same reference numerals thereto, and only different points will be described.

Figure 15:
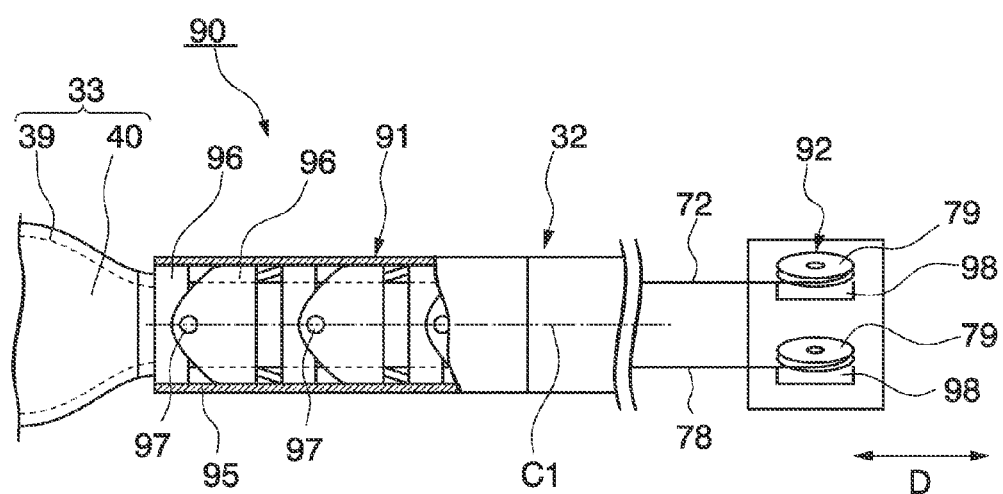
FIG. 15 is a plan view of essential parts of an endoscope holding device of a third embodiment of the invention.

As shown in FIG. 15, an endoscope system of the present embodiment includes an overtube 90 that is the endoscope holding device, instead of the overtube 30 of the endoscope system 1 of the first embodiment.

The insertion part 32 of the overtube 90 has a curving portion 91 capable of being curved in the longitudinal direction D at its own distal end side, and the proximal end of the insertion part 32 is provided with a manipulating part 92 capable of fixing the curving portion 91 in a predetermined curving state.

The curving portion 91 has curving pieces 96 and a plurality of manipulation wires 78 which the distal end is connected to the curving pieces 96. The curving pieces 96 have a well-known configuration, are arranged within a sheath tube 95, and are arranged parallel to the center axis C1 of the lumen 31.

The curving pieces 96 are formed in a substantially tubular shape and made from a hard material, such as stainless steel. The curving pieces 96 adjacent to the center axis C1 are connected by pivoting members 97 so as to be rotatable to each other. The curving portion 91 can be curved in a desired direction with respect to the longitudinal direction D. The distal ends of the manipulation wires 78 are connected to the curving pieces 96 located at the foremost end, and extend parallel to the longitudinal direction D.

The manipulating part 92 has the pulleys 79 connected to the proximal ends of the manipulation wires 78, respectively, and ratchet mechanisms 98 connected to the pulleys 79. The ratchet mechanism 98 can hold the position of the pulley 79 that has rotated at a desired angle of rotation, and can release this holding.

According to the endoscope system of the present embodiment configured in this way, the overtube 90 and the endoscope insertion part 11 can be compactly integrated with each other.

Moreover, the overtube 90 has the curving portion 91 and the manipulating part 92. Therefore, the curving portion 91 that are brought into a predetermined curving state by pulling the manipulation wires 78 by the manipulating part 92 can be fixed by the ratchet mechanisms 98. Thereby, the overtube 90 can be manipulated as if the whole curving portion 91 is made from a hard material. That is, a force applied to the proximal end of the overtube 90 that is brought into a predetermined curving state can be reliably transmitted toward the distal end.

Furthermore, the curving portion 91 can be curved in a desired shape by releasing the holding by the ratchet mechanisms 98 and manipulating the manipulating part 92.

While preferred embodiments of the invention have been described and illustrated above, it should be understood that these are exemplary of the invention and are not to be considered as limiting. Additions, omissions, substitutions, and other modifications of components can be made without departing from the spirit or scope of the present invention.

For example, in the first to third embodiments, the plate-like body 40 is made from a material having light permeability. However, this is not essential, and the plate-like body may be made from a material that cuts off light, such as metal. This is because there is a case where the field of view in front of the endoscope insertion part 11 has no importance, like a case where the size of the plate-like body is relatively small.

Additionally, in the first to third embodiments, the endoscope curving portion 13 capable of being curved is provided at the distal end of the endoscope insertion part 11. However, when the distal end of the endoscope insertion part is provided with a distal end hard portion that is not curved and has a certain length, and an endoscope curving portion capable of being curved is connected to a proximal end of the distal end hard portion, the length of the part of the spatula part 33 in front of the distal end face of the insertion part 32 may be equal to or more than the sum total of the length of the distal end hard portion, and the length (curving length) of the portion in front of the distal end face of the insertion part 32 of the endoscope curving portion.

Although the scales 18 are used as indexes in the first to third embodiments, the indexes are not limited to the scales. For example, marks, such as arrows, may be adopted. Moreover, for example, when the length by which the endoscope insertion part 11 is inserted into the lumen 31 can be detected by a length measuring device or the like, it is not necessary to provide the endoscope insertion part 11 with the indexes.

The case where the rectum is incised by the endoscope system to perform a procedure has been described in the first to third embodiments. However, the portion to be incised is not limited to the rectum, and may be, for example, an alimentary canal wall, such as a stomach wall, a vagina, or an abdominal wall. Additionally, the internal organ to be displaced is not limited to the liver, and may be internal organs within the abdominal cavity, such as the stomach, the spleen, and the intestines.

Figure 16A:
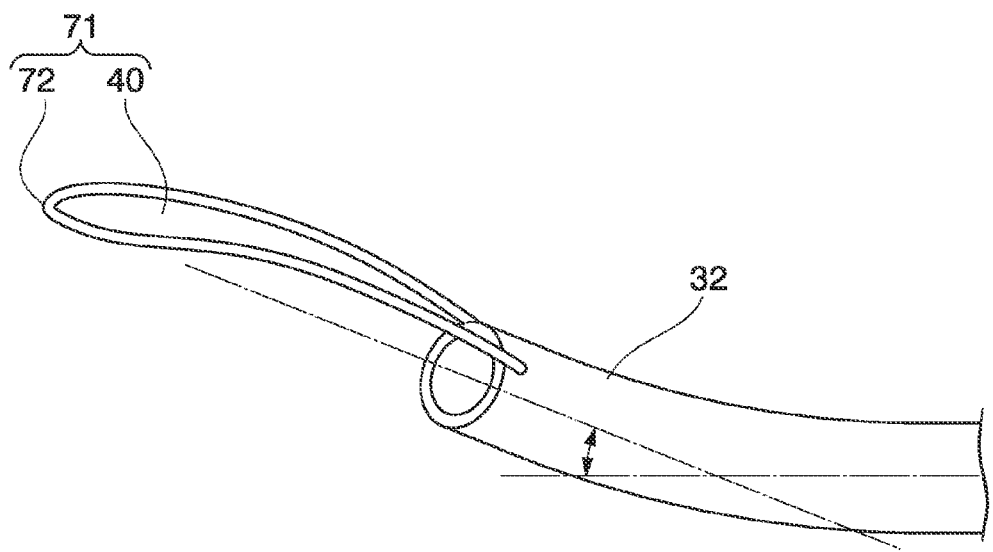
FIG. 16A is a diagram showing that the endoscope holding device related to the embodiment of the invention is bent.
Figure 16B:
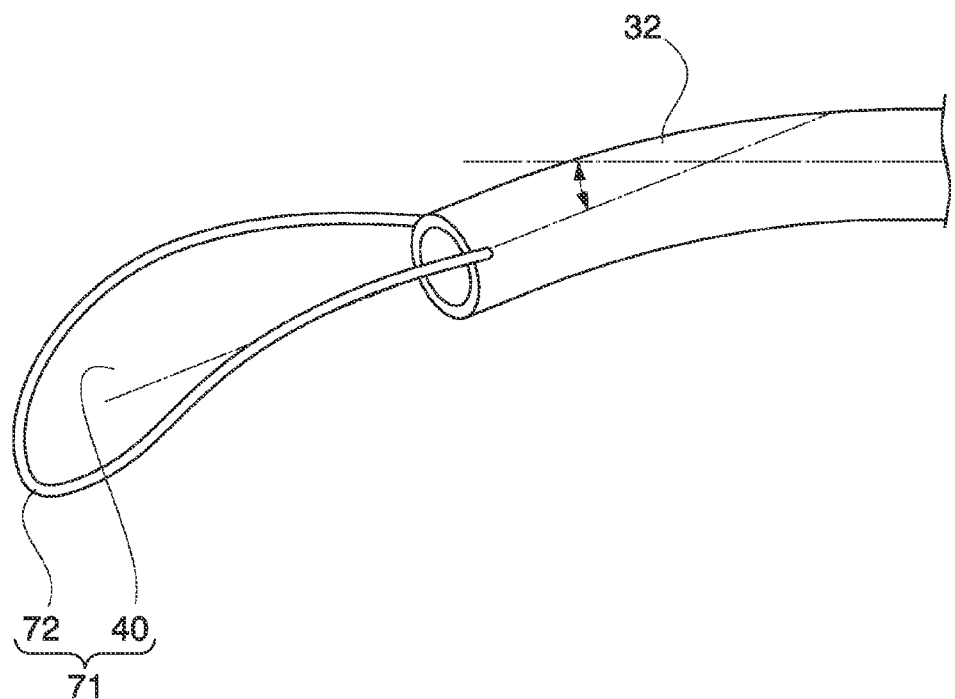
FIG. 16B is a diagram showing that the endoscope holding device related to the embodiment of the invention is bent.

In addition, as described in FIGS. 16A and 16B, the distal end side of the insertion part 32 may be bent in advance within a virtual plane (plane parallel to the surface of a sheet) that intersects a displacement plane, or may be bendable or curvable. By adopting this structure, the space for performing a procedure is easily secured at a position in a direction opposite to a displacement direction when a tissue is displaced.

The invention claimed is:

1. An endoscope holding device comprising:
   an insertion part having an insertion passage into which an endoscope insertion part is capable of being inserted, the insertion part being capable of holding the endoscope insertion part so as to freely protrude and retract from a distal end face of the insertion part;
   a displacement part having a proximal end portion, which is affixed to a distal end portion of the insertion part, and a distal end portion which protrudes from the distal end portion of the insertion part toward a far end side than the end portion of the insertion part; and
   a locking portion provided at the distal end portion of the displacement part and capable of holding a distal end of the endoscope insertion part that protrudes from the distal end face of the insertion part, wherein
   the displacement part comprises:
      a frame body formed in a shape of an arch that, in a side view, is convex in a direction apart from a center axis of the insertion passage, and
      a plate-like body which is provided so as to occlude a part of a space formed at a center of the frame body and which includes a cut out portion formed at a distal end of the plate-like body, wherein
   the locking portion is configured to be capable of holding the endoscope insertion part such that the distal end of the endoscope insertion part passes through a displacement face of the displacement part at the cut out portion, and
   the displacement part is configured to be capable of displacing a living body tissue in a state where the endoscope insertion part is held with the locking portion; and
   a distal end face of the endoscope insertion part being held with the locking portion is directed in a same direction as the distal end face of the insertion part.

2. The endoscope holding device according to claim 1, wherein the plate-like body is formed so as to be larger than the external diameter of the insertion part in a width direction of the plate-like body specified in a protruding direction of the endoscope.

3. The endoscope holding device according to claim 1, wherein an airtight valve is provided within the insertion passage.

4. The endoscope holding device according to claim 3, wherein the locking portion is a through hole formed at a distal end of the displacement part.

5. The endoscope holding device according to claim 3, wherein the through hole is formed with a size such that the insertion part is capable of being inserted thereinto.

6. The endoscope holding device according to claim 3, wherein the through hole is provided on a center axis of the insertion passage at a distal end of the insertion passage.

7. The endoscope holding device according to claim 3, wherein the insertion part has a curving portion capable of being curved in a longitudinal direction of the insertion part, and a manipulating part which is configured to fix the curving portion in a predetermined curving state.

8. The endoscope holding device according to claim 3, wherein the displacement part has the frame body formed from a hard material and has a plate-like body that occludes at least a part of a space formed at a center of the frame body.

9. The endoscope holding device according to claim 8, wherein the plate-like body is formed such that a range occupied by the plate-like body includes a range occupied by an inner cavity of the insertion part, in the width direction of the plate-like body, as seen from a direction parallel to the center axis of the insertion part.

10. The endoscope holding device according to claim 3, wherein the intermediate portion of the displacement part is arranged at a position farther from the center axis of the insertion passage than the proximal end portion of the displacement part in the longitudinal direction of the insertion part.

11. The endoscope holding device according to claim 3, wherein an outer periphery of the displacement part is formed to be equal to or more than a predetermined curvature radius, and an outer periphery of a cross-section of the displacement part orthogonal to the longitudinal direction of the insertion part is formed to be equal to or more than the predetermined curvature radius, as seen from a direction orthogonal to the center axis of the insertion part.

12. The endoscope holding device according to claim 3, wherein the displacement part is configured so as to be rotatable around an axis that intersects the center axis of the insertion part.

13. The endoscope holding device according to claim 3, wherein the locking portion is formed at a position apart by a predetermined distance forward from an opening portion which opens at the distal end part of the insertion part in communication with the insertion passage.

14. An endoscope system comprising:
the endoscope holding device according to claim 3, and an endoscope which has an endoscope insertion part capable of being inserted into the insertion passage of the endoscope holding device, wherein
the endoscope insertion part has an endoscope curving portion capable of being curved to a distal end thereof, and a length of the displacement part in a longitudinal direction of the insertion part is made equal to or more than a curving length of the endoscope curving portion.

15. The endoscope system according to claim 14, wherein indexes are provided in the longitudinal direction of the endoscope insertion part in the endoscope insertion part.

16. The endoscope holding device according to claim 1, wherein the displacement part is formed in the shape of an arch that is convex in the radially outward direction.

* * * * *